United States Patent
Hu et al.

(10) Patent No.: US 9,421,224 B2
(45) Date of Patent: Aug. 23, 2016

(54) METHOD OF INDUCING AUTOPHAGY AND ACTIVATING TOLL-LIKE RECEPTOR

(71) Applicant: National Tsing Hua University, Hsinchu (TW)

(72) Inventors: Yu-Chen Hu, Hsinchu (TW); Guan-Yu Chen, Hsinchu (TW); Hsing-Yu Tuan, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 64 days.

(21) Appl. No.: 14/622,457

(22) Filed: Feb. 13, 2015

(65) Prior Publication Data

US 2015/0157659 A1 Jun. 11, 2015

Related U.S. Application Data

(62) Division of application No. 13/913,716, filed on Jun. 10, 2013.

(51) Int. Cl.
*A61K 33/00* (2006.01)
*A61K 31/194* (2006.01)
*A61K 9/00* (2006.01)
*A61K 9/14* (2006.01)

(52) U.S. Cl.
CPC ............ *A61K 33/00* (2013.01); *A61K 9/0019* (2013.01); *A61K 9/14* (2013.01); *A61K 31/194* (2013.01)

(58) Field of Classification Search
None
See application file for complete search history.

(56) References Cited

PUBLICATIONS

Markovic et al., Graphene quantum dots as autophagy-inducing photodynamic agents, 2012, Biomaterials, 33, 7084-7092.*
Zabirnyk, nanoparticles as a novel class of autophagy activators, 2007, autophagy, online, 1554-8635.*
Guan-Yu Chen et al., "Simultaneous induction of autophagy and toll-like recepto signaling pathways by graphine oxide", *Biomaterials* 33 (Jun. 15, 2012) pp. 6559-6569.

* cited by examiner

*Primary Examiner* — Mina Haghighatian
*Assistant Examiner* — Luke Karpinski
(74) *Attorney, Agent, or Firm* — Muncy, Geissler, Olds & Lowe, P.C.

(57) ABSTRACT

A method of inducing autophagy in a cell is achieved by contacting the cell with graphene oxide (GO) in an amount effective to induce autophagy in the cell, wherein the cell expresses at least one of TLR-4 (Toll-like receptor 4) and TLR-9 (Toll-like receptor 9). Differences between autophagy triggered by GO and other conventional agonists such as rapamycin have been observed. GO may activate autophagy in some cells that may not be triggered by rapamycin. The cell reveals no apparent apoptosis after treatment of the graphene oxide. A method of activating a Toll-like receptor in a cell is also herein provided.

9 Claims, 15 Drawing Sheets

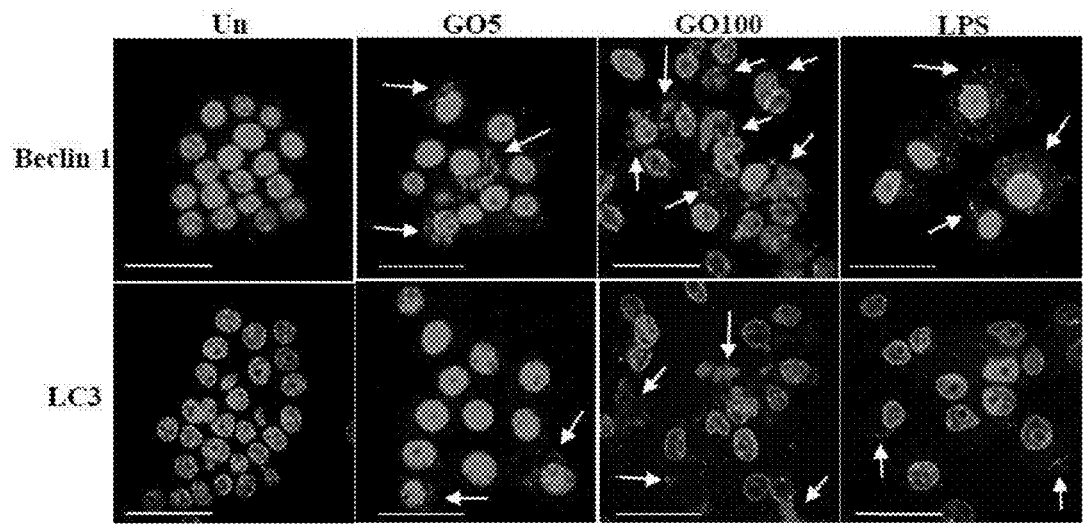
Fig. 3A
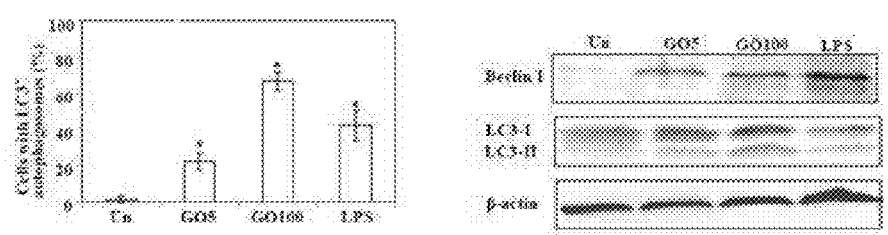
Fig. 3B
Fig. 3C

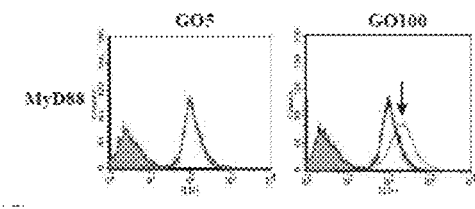 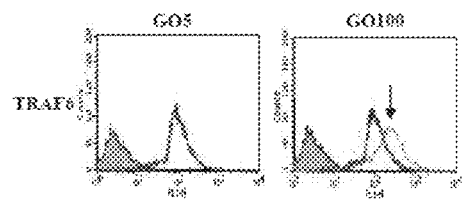
Fig. 6A          Fig. 6B
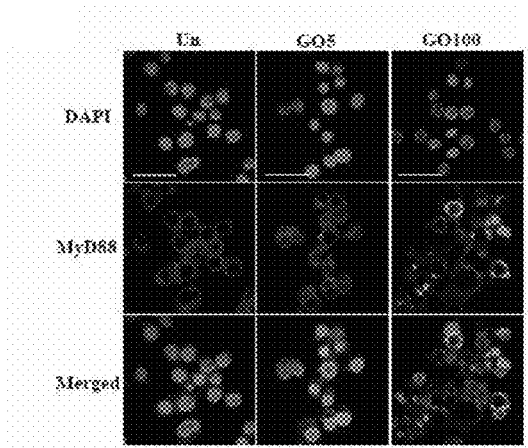 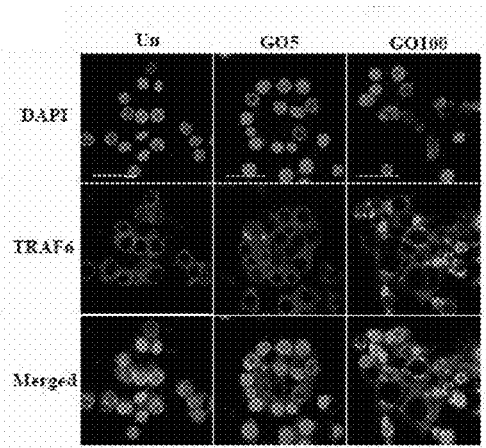
Fig. 6C          Fig. 6D
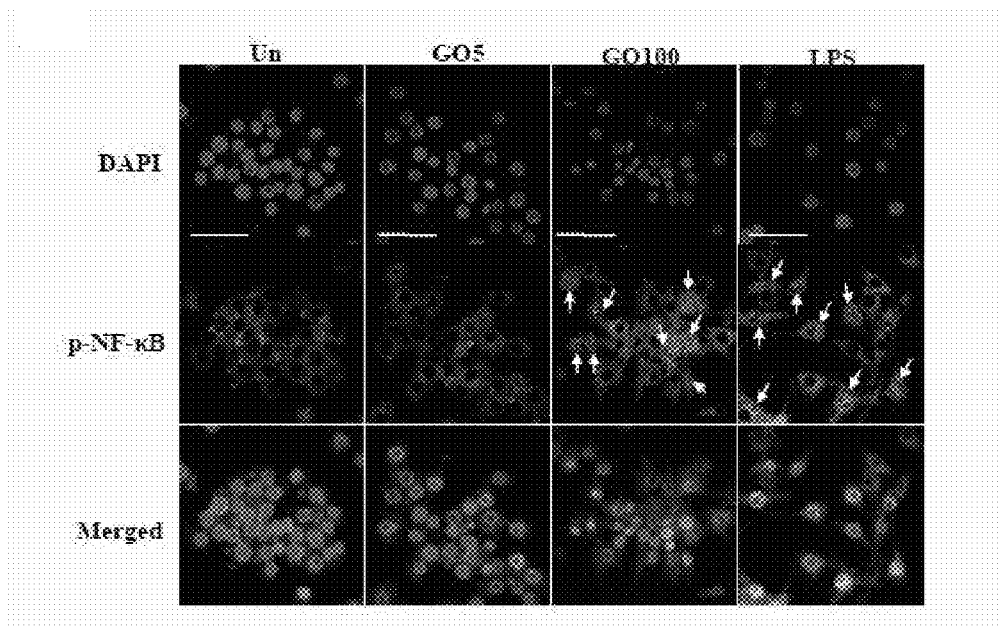
Fig. 6E

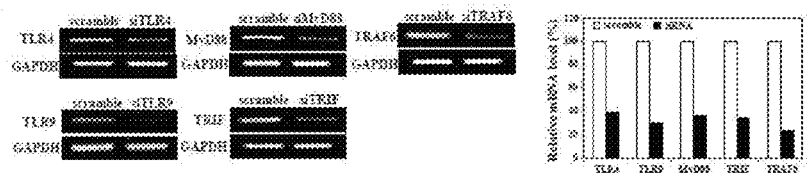
Fig. 7A                    Fig. 7B
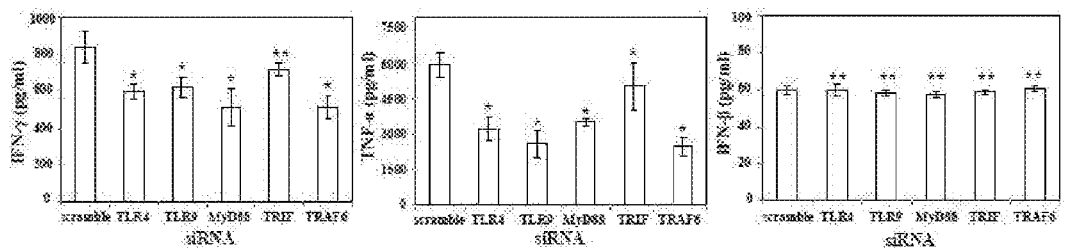
Fig. 7C
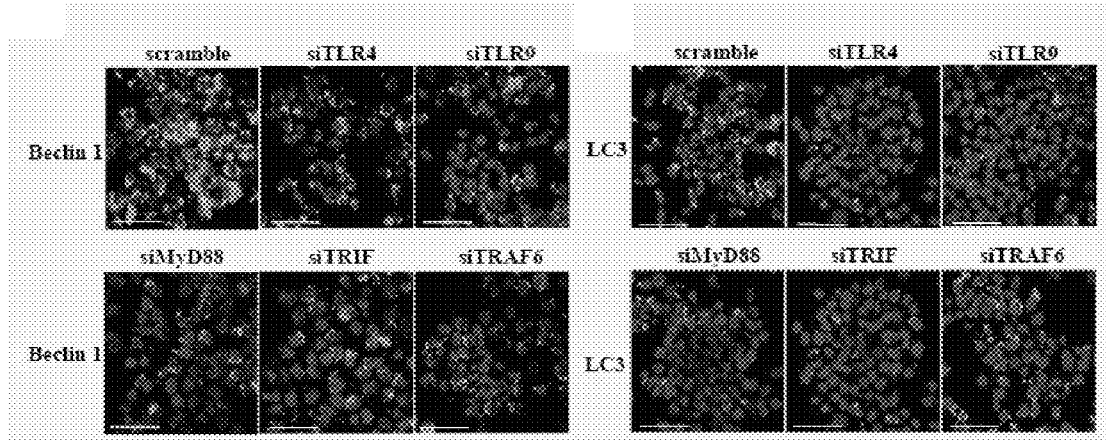
Fig. 7D                                   Fig. 7E
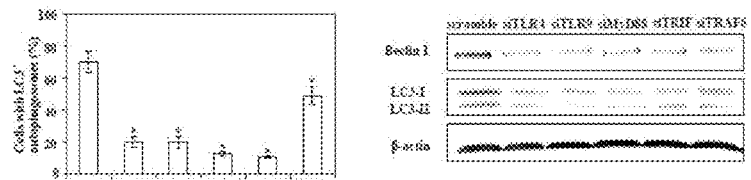
Fig. 7F         Fig. 7G

METHOD OF INDUCING AUTOPHAGY AND ACTIVATING TOLL-LIKE RECEPTOR

CROSS REFERENCE TO RELATED APPLICATIONS

This application is a Divisional of co-pending application Ser. No. 13/913,716, filed on Jun. 10, 2013, for which priority is claimed under 35 U.S.C. §120, the entire contents of all of which are hereby incorporated by reference.

BACKGROUND OF THE INVENTION

1. Field of the Invention

The present invention relates to a method of inducing autophagy in a cell, particularly to a method of inducing autophagy in a cell by activating Toll-like receptors.

2. Description of the Prior Art

Graphene and its oxidized form, graphene oxide (GO), have drawn intense attention in recent years for biological and medical applications. The surface of GO contains hydrophilic oxygen-containing functional groups (i.e. hydroxyl, epoxyl and carboxyl tails) on the basal plane and edges, rendering GO amenable to stable dispersion in water and functionalization. These attributes have prompted the use of GO for bioimaging, cellular probing, cellular growth and differentiation, gene and drug delivery and photothermal therapy. These burgeoning applications in biomedicine entail the need to evaluate the in vitro and in vivo safety of GO.

Autophagy is a process that degrades intracellular components in response to stressful conditions (e.g. starvation and infection) and is linked to cellular processes as diverse as cell survival, cell death, pathogen clearance and antigen presentation. Autophagy involves the formation of double-membraned vesicles termed autophagosomes, which sequester cytoplasm and organelles and then fuse with lysosomes to form autolysosomes, thus degrading the contents of the vacuole. Autophagy is negatively controlled by mTOR (mammalian target of rapamycin) complex 1 (mTORC1) and inhibition of mTORC1 kinase activity initiates the formation of autophagosome that comprises a complex consisting of Beclin 1 and other factors. The autophagosome formation also involves the conversion of microtubule-associated protein light chain 3 (LC3-I) to the lipidated form LC3-II, consequently conversion from LC3-I to LC3-II is a common indicator of autophagy.

Toll-like receptors (TLRs) are important receptors for the detection of microbial antigens and subsequent induction of innate immune responses. Among the TLRs, TLR2 recognizes bacterial lipoproteins while TLR3 detects virus-derived dsRNA. TLR4 recognizes lipopolysaccharides (LPS) and TLR5 recognizes bacterial flagellin. TLR7 mediates recognition of viral ssRNA while TLR9 senses unmethylated DNA with CpG motifs derived from bacteria and viruses. Upon engagement with cognate ligands, the TLRs transduce signals by first recruiting adaptor proteins including myeloid differentiating factor 88 (MyD88) and TIR domain-containing adaptor inducing IFN-beta (TRIF), followed by activation of downstream signaling proteins such as TRAF6 and NF-κB, eventually resulting in various cellular responses including secretion of cytokines and interferons (IFNs).

The connection between autophagy and TLRs was discovered in 2007 as it was found that TLRs signaling in macrophages links the autophagy pathway to phagocytosis and TLR4 stimulation enhances the autophagic elimination of phagocytosed mycobacteria in macrophages. Ensuing studies further reported that TLR2, TLR3 and TLR7 play roles in autophagy induction. To date the precise mechanisms regulating the TLRs-elicited autophagy remain to be established although agonists stimulating TLR2, TLR3, TLR4 and TLR7 were shown to trigger autophagy.

SUMMARY OF THE INVENTION

The present invention is directed to provide a new mechanism by which cells respond to nanomaterials and underscores the importance of future safety evaluation of nanomaterials.

According to an embodiment, A method of inducing autophagy in a cell is achieved by contacting the cell with graphene oxide (GO) in an amount effective to induce autophagy in the cell, wherein the cell expresses at least one of TLR-4 (Toll-like receptor 4) and TLR-9 (Toll-like receptor 9).

According to another embodiment, a method of activating a Toll-like receptor in a cell is achieved by contacting the cell with graphene oxide in an amount effective to activate a at least one of TLR-2 (Toll-like receptor 2), TLR-4 (Toll-like receptor 4), TLR-7 (Toll-like receptor 7) and TLR-9 (Toll-like receptor 9) in the cell, whereby at least one of TLR-2, TLR-4, TLR-7 and TLR-9 are activated in the cell.

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein:

FIG. 3A are Immunofluorescence microscopy illustrating Beclin 1 and LC3 activation of GO5 and GO100;

FIG. 3B are Quantitative analysis of immunofluorescence micrographs showing cells with LC3+ dots;

FIG. 3C are Western blot illustrating the expression of Beclin 1, LC3-I and LC3-II;

FIG. 6A-6B are flow cytometry outcomes illustrating upregulated the expression of MyD88 and TRAF6;

FIG. 6C-6D are immunofluorescence microscopy illustrating upregulated the expression of MyD88 and TRAF6;

FIG. 6E is immunofluorescence microscopy illustrating the activation and nuclear translocation of phosphorylated NF-κB;

FIG. 7A-7B are RT-PCR outcomes of macrophage cells treated with siRNA specific for TLR4, TLR9, MyD88, TRIF or TRAF6;

FIG. 7C is ELISA analysis depicting that silencing TLR4, TLR9, MyD88 and TRAF6 attenuated the IFN-γ and TNF-α expression;

FIG. 7D is Immunofluorescence microscopy further illustrating that silencing TLR4, TLR9, TRIF, MyD88 and TRAF6 abolished the GO-induced formation of Beclin 1 aggregates;

FIG. 7E-7F are immunofluorescence microscopy and quantitative analysis illustrating inhibition of GO-induced LC3+ aggregates also occurred after silencing TLR4, TLR9, TRIF, MyD88 and TRAF6;

FIG. 7G is Western blot illustrating that suppression of Beclin 1 expression and LC3-I conversion to LC3-II by gene silencing;

DESCRIPTION OF THE PREFERRED EMBODIMENT

Figure 1A:
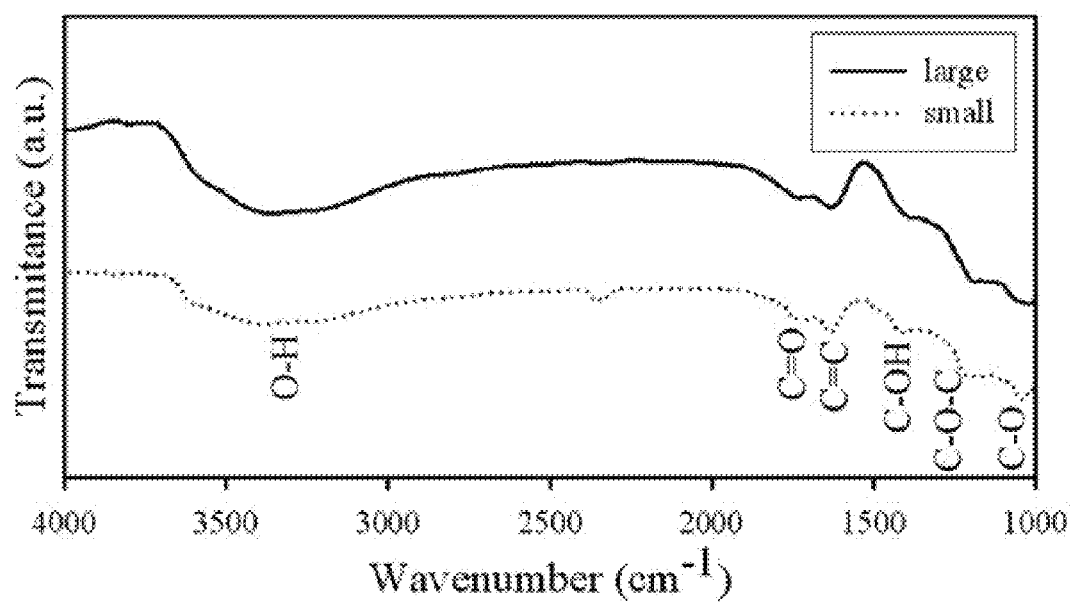
FIG. 1A is a diagram illustrating characteristic peaks of oxygen-containing groups for both large and small GO.

The present invention demonstrated that treatment of cells with GO simultaneously triggers autophagy and mainly TLR4/TLR9-regulated inflammatory responses.

In one embodiment, the particle sizes of the graphene oxide may range from 100 nm to 3 μm, preferably 100 nm to 800 nm and average around 450 nm. The concentration of the graphene oxide may be greater than or equal to 5 μM, preferably greater than or equal to 50 μM or 100 μM.

Autophagy triggered by GO have been observed in various types of cells such as cancer cells and immune cells. In one preferred embodiment, cancer cells may include an ovarian cancer cell (SKOV3), a brain can cell (ALTS1C1), a prostate cancer cell (Tramp C1), a cervical cancer cell (HeLa), a lung cancer cell (A549), a liver cancer cell (Mahlavu) or a colon cancer cell (CT26). Immune cells may include primary immune cells such as macrophages.

In addition, differences between autophagy triggered by GO and other conventional agonists such as rapamycin have been observed. GO may activate autophagy in some cells that may not be triggered by rapamycin. Some cells are likely damaged by rapamycin in comparison to GO treatment. The cell reveals no apparent apoptosis or necrosis after treatment of the graphene oxide. Furthermore, the autophagy induced by GO may be more than 40% of the cell. In one preferred embodiment, autophagy may be induced in essentially 80% or more of the cell.

The autophagy presented by the present invention was at least partly regulated by the TLRs pathway. Very importantly, TLRs are well known detectors for various biological molecules, but their sensing of non-living nanomaterials such as GO has yet to be reported. Neither has any study documented that nanomaterials can induce autophagy via the regulation of TLRs. This present invention thus presents a new mechanism by which cells respond to nanomaterials and underscores the importance of future safety evaluation of nanomaterials.

The detailed explanation of the present invention is described as follows. The described preferred embodiments are presented for purposes of illustrations and description, and they are not intended to limit the scope of the present invention.

Reference of Chen et al. (Biomaterials 33 (2012) 6559-6569, hence abbreviated as Reference) is herein incorporated by reference in its entirety.

Preparation and Characterization of GO

Large GO with a size of ≈2.4 μm was prepared from natural graphite (Bay Carbon, SP-1, average particle size ≈30 μm) by the modified Hummers method as described previously [20] and dispersed in water. The solution was centrifuged (7,200×g for 5 min) to remove unexfoliated GO and byproducts and centrifuged again (400×g for 15 min) to remove broken fragments and debris. The pellet was dried under vacuum overnight to yield the large GO, weighed on a Sartorius SE2 ultra-micro balance with 0.1 µg resolution and dissolved in deionized water to a final concentration of 250 µg/ml. Small GO with a size of ≈350 µm was prepared via tip sonication (Misonix Sonicator 3000) of the large GO solution in an ice bath at a power of 30 W for 1 h, filtered through a 0.45 µm syringe filter (Sartorius Stedim Biotech) and dried under vacuum overnight. The small GO was weighed and dissolved in water to a desired concentration.

The surface morphology of GO was characterized with an atomic force microscope (AFM, XE-70, Park System) in tapping mode using the aluminum coating silicon probe (frequency 300 kHz, spring constants 40 N/m, scanning rate 1 Hz), under ambient conditions and scanning line of 512. High-resolution X-ray photoelectron spectroscopy (HRXPS) and attenuated total reflectance HRXPS were performed on a Kratos Axis Ultra DLD using a focused monochromatic Al X-ray source (1486.6 eV). The Fourier transform infrared (ATR-FTIR) spectra of GO were recorded using a Perkin-Elmer Spectrum RXI FTIR spectrometer with 2 $cm^{-1}$ resolution and 32 scans, and the background was collected in the absence of samples. The size distribution of GO was characterized by using Dynamic Light Scattering (380 ZLS, Nicomp, USA) from Particle Sizing Systems at room temperature.

Cell Culture and Treatment with GO

The mouse macrophage cell line RAW264.7 was maintained in Dulbecco's modified Eagles medium (DMEM, Gibco) containing 10% fetal bovine serum (FBS, Gibco) and subcultured upon 70-80% confluency. For GO treatment, the cells were seeded to 6-well plates ($3\times10^5$ cells/$cm^2$) overnight and cultured using the medium supplemented with GO at final concentrations of 5 or 100 µg/ml for 24 h. In parallel, the cells were treated with LPS (10 µg/ml, Sigma) for 24 h as the positive control. After the treatment, the cell morphology and vacuoles were observed under the phase contrast microscope.

Transmission Electron Microscopy (TEM)

The cells were harvested, centrifuged (215×g, 10 min), washed with cold PBS and fixed with 2.5% glutaraldehyde (in 0.2 M sodium cacodylate, pH 7.4). The samples were then fixed in 1% $OsO_4$ for 1 h at 4° C., dehydrated with increasing concentrations of ethanol, embedded in spur resin and sectioned. The ultrathin sections were stained with uranyl acetate and observed under the TEM.

Immunofluorescence Microscopy

The cells were fixed and permeabilized as described previously [4], followed by extensive washing and primary antibody staining (1:100 dilution) for 1 h at 4° C. in the dark. The primary antibody was specific for LC3 (4108, Cell Signaling Technology), Beclin 1 (ab55878, Abcam), TLR4 (14-9924, eBioscience), TLR9 (ab17236, abcam), MyD88 (ab2068, abcam), TRAF6 (ab33915, abcam), phosphorylated NF-κB (3033, Cell Signaling Technology) or IRF3 (sc-15991, Santa Cruz Biotechnology). After washing, the cells were incubated with the goat anti-mouse antibody conjugated with Alexa 488 (for TLR9, Invitrogen), goat anti-rabbit antibody conjugated with Alexa 488 (for LC3, MyD88, TRAF6 and NF-κB, Invitrogen) or donkey anti-goat IgG conjugated with Dylight 488 (for IRF3, Jackson ImmunoResearch) for 1 h at 4° C. in the dark. After washing, the cells were counterstained with 4,6-diamidino-2-phenylindole (DAPI, Vector Labs) and visualized with a confocal microscope (Nikon TE2000 equipped with the confocal upgrade laser kit). Fifty to one hundred cells in the images for LC3 were counted for quantification of LC3+ cells.

ELISA and Western Blot

At 24 h post-treatment, the supernatant was collected from the GO-treated cell culture and analyzed using ELISA kits specific for mouse IL-2, IL-10, TNF-α, IFN-β and IFN-γ. The cells were lysed for Western blot using primary antibodies (1:1000 dilution) specific for LC3, Beclin 1 or β-actin (A-2066, Sigma) and the secondary antibody was HRP-conjugated IgG (1:5000 dilution, Amersham Biosciences). The images were developed using the GeneGnome HR scanner (Syngene).

Reverse Transcription-Polymerase Chain Reaction (RT-PCR)

Total RNA was extracted from the cells using the Nucleo-Spin® RNA II purification kit (Clontech) and reverse transcribed to cDNA using the MMLV Reverse Transcriptase 1 st-Strand cDNA Synthesis Kit (Epicentre Biotechnologies). The RT-PCR reactions were performed using Taq DNA polymerase (Promega) in the Px2 Thermal Cycler (Thermo Electron) under the condition of 30 s at 95° C., 45 s at 60° C. and 30 s at 72° C., and the amplicons were subjected to 2% agarose gel electrophoresis. For TLRs transcription analysis, the cDNA was amplified using the Murine TLR RT-Primers (Invivogen).

Flow Cytometry

The cells were fixed and permeabilized with 4% formaldehyde and 0.5% Tween-20. After washing, the cells were incubated with the primary antibody (1:100 dilution) for 1 h at 4° C. in the dark. For TLR2 and TLR4 detection, the primary antibody was Alexa 488-conjugated MAb specific for mouse TLR2 (53-9024, eBioscience) or PE-conjugated MAb specific for mouse TLR4 (12-9924, eBioscience). For TLR7, TLR9, MyD88 and TRAF6 detection, the cells were incubated with the primary antibody specific for mouse TLR7 (ab45371, abcam), TLR9 (ab17236, abcam), MyD88 (ab2068, Abcam) or TRAF6 (ab33915, Abcam) and then incubated with Alexa 488-conjugated goat anti-rabbit (for TLR7, MyD88 and TRAF6) or goat anti-mouse (for TLR9) IgG for 1 h at 4° C. in the dark. After washing, the cells were collected for flow cytometry (FACSCalibur, BD Biosciences) analyses.

Gene Knockdown by Small Interfering RNA (siRNA)

To knockdown specific genes, macrophages cells were transfected with 5 µg of scramble siRNA (SC-36869, Santa Cruz Biotechnology) or siRNA specific for TLR4, TLR9, MyD88, TRAF6 or TRIF (Santa Cruz Biotechnology). At 48 h post-transfection, cells were treated with GO or LPS as described above. The supernatant was collected 24 h later for ELISA and the cells were harvested for immunofluorescence microscopy and Western blot. Statistical analysis All data represented the mean±standard deviation of at least 3 independent culture experiments. The data were statistically analyzed by one-way ANOVA. $p<0.05$ was considered significant.

Example 1

Preparation and Characterization of Large and Small GO Nanosheets

Figures 1B, 1C:
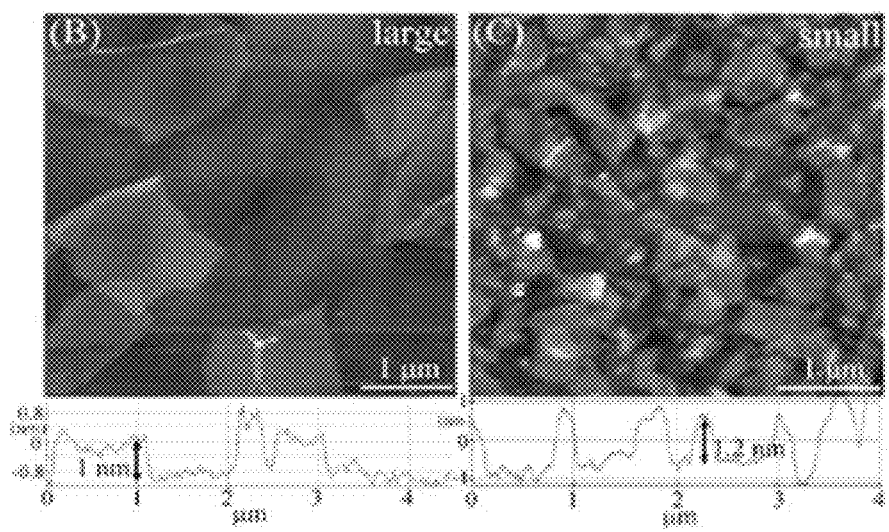
FIG. 1B-1C are Atomic force microscopy (AFM) images showing significant difference of lateral dimensions between large and small GO.
Figure 1D:
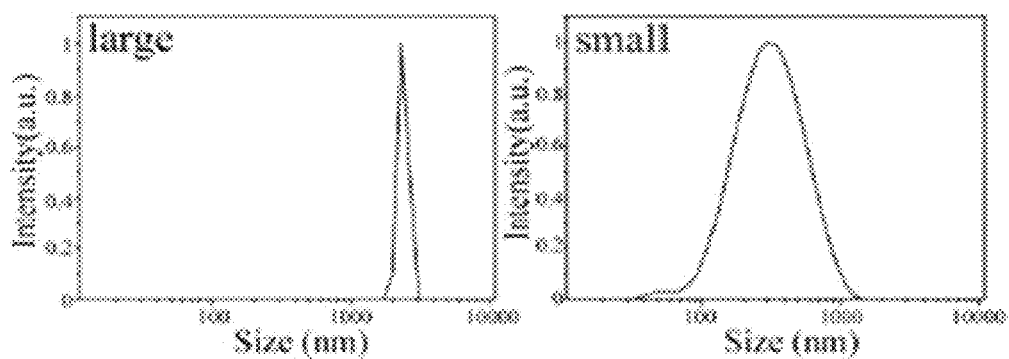
FIG. 1D is a diagram illustrating hydrodynamic diameters of large and small GO.

Large-size GO was prepared from natural graphite by the modified Hummers method while small-size GO was obtained by sonicating large GO into smaller pieces via tip sonication. Atomic force microscopy (AFM) images showed significant difference of lateral dimensions between large and small GO (FIG. 1B-1C). The thicknesses of both large and small GO measured ≈1.0-1.2 nm, which agreed with the GO thickness reported previously and indicated the formation of single-layer GO. The GO was thicker than graphene (≈20.34 nm) due to the surface functional groups. The effective hydrodynamic diameters of large and small GO were ≈2.4 µm and ≈350 nm, respectively, as measured by Dynamic Light Scattering (FIG. 1D). The surface states of large and small GO were identical as demonstrated by high-resolution C 1 s XPS spectra (not illustrated), in which the 4 peaks centering at 285, 286.4, 287.1 and 289.0 eV corresponded to C=C/C≡C in the non-oxygenated aromatic rings, C—O (epoxy and alkoxy), C=O, and O=C—O groups, respectively. The FTIR spectra (FIG. 1A) also delineated the same characteristic peaks of oxygen-containing groups for both large and small GO.

Example 2

GO Nanosheets Induced Autophagy in a Dose-Dependent Manner

Figure 2A:
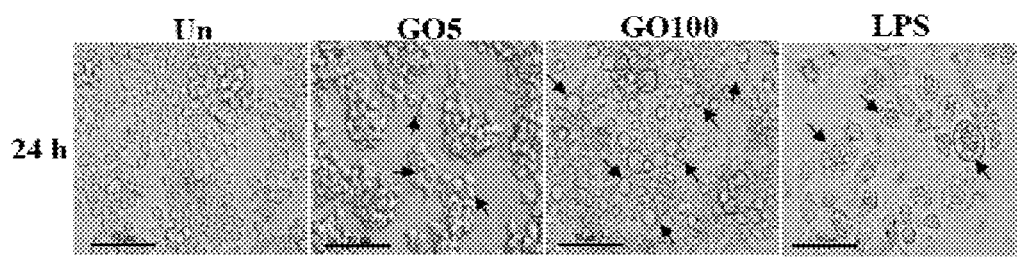
FIG. 2A is a microscopy illustrating the formation of small vacuoles inside the cells induced by GO at 24 h post-incubation.

To examine how GO nanosheets influenced the macrophage, RAW264.7 cells were incubated with small GO at either 5 µg/ml (designated as GO5 group) or 100 µg/ml (designated as GO100 group) for 24 h. In comparison with the untreated control, GO5 induced the formation of small vacuoles inside the cells at 24 h post-incubation (FIG. 2A) but did not cause apparent cell death (FIG. S1A of reference). Increasing the small GO concentration to 100 µg/ml (GO100 group) gave rise to more evident vacuole formation (FIG. 2A) and significant cell death (FIG. S1A of reference), which were also observed in the LPS-treated cells (10 µg/ml). However, GO treatment did not elicit discernible apoptosis as illustrated by TUNEL assays (FIG. S1B of reference). Similar vacuoles were also observed in the cells treated with large GO (FIG. S2A of reference).

Figure 2B:
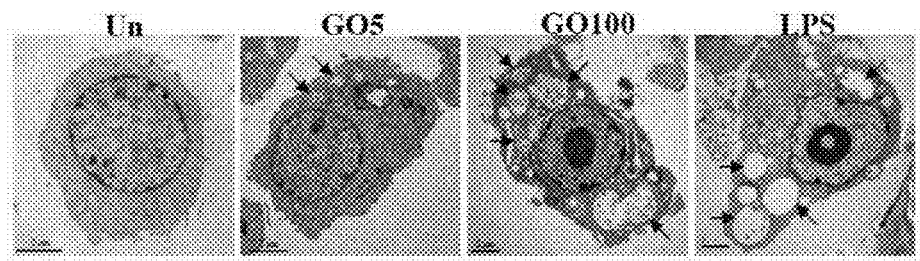
FIG. 2B-2C are transmission electron microscopy demonstrating that GO5 evoked the appearance of some autophagic vacuoles (AV) while GO100 and LPS triggered more prominent AV.
Figure 2C:
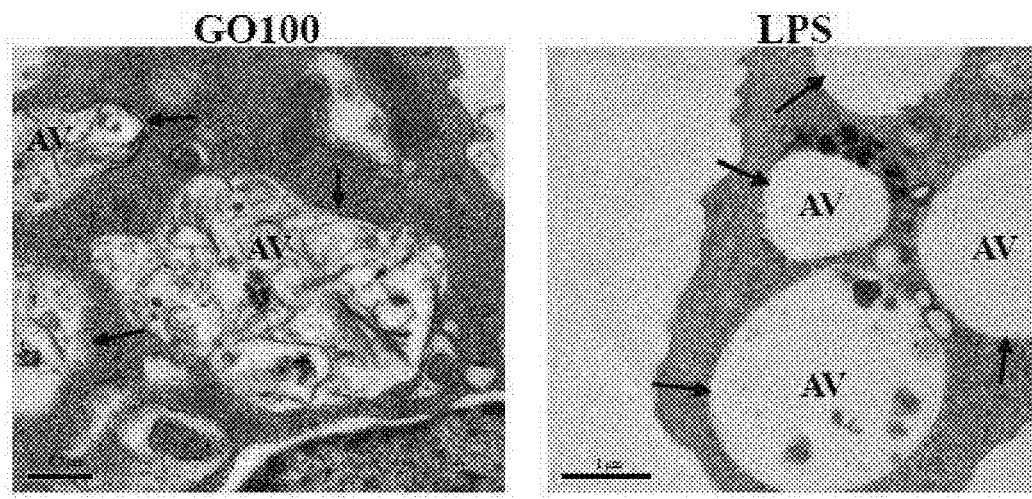
Figure 4A:
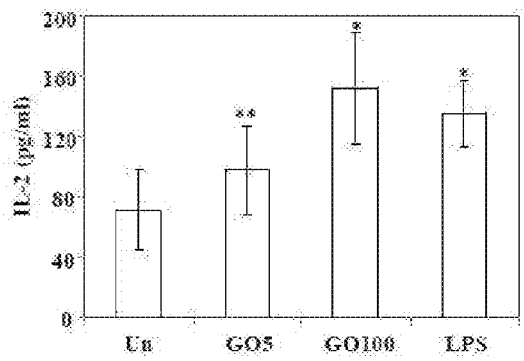
FIG. 4A-4E are ELISA analyses depicting that treatment of macrophage cells with small GO at 100 μg/ml significantly induced the production of IL-2, IL-10, IFN-γ and TNF-α but not IFN-β when compared with the untreated cells.
Figure 4B:
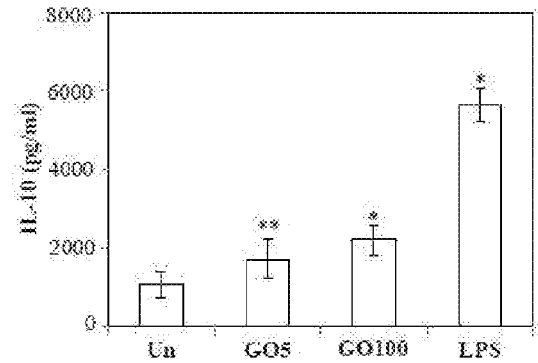
Figure 4C:
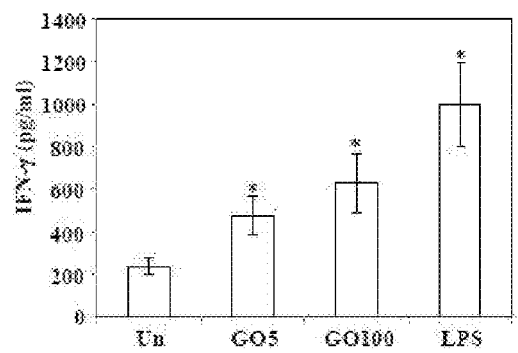
Figure 4D:
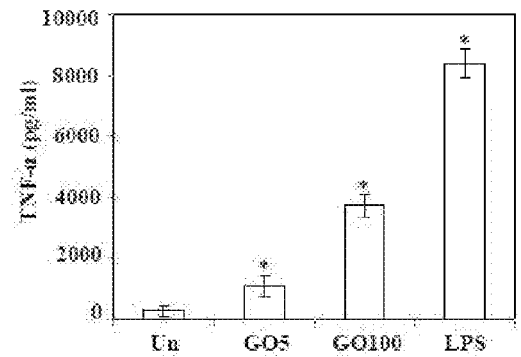
Figure 4E:
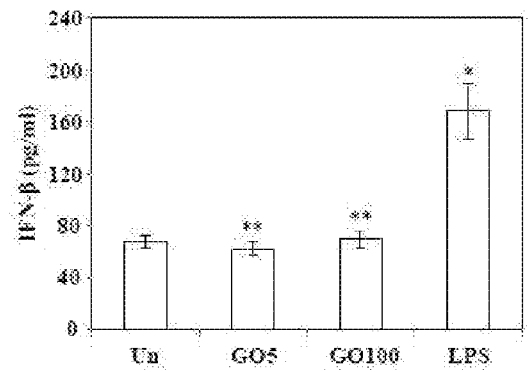

Since the GO-induced vacuoles were observed in cells treated with LPS, a ligand that induces both autophagy and TLR pathway, we surmised that GO triggered autophagy. Indeed, the transmission electron microscopy demonstrated that GO5 evoked the appearance of some autophagic vacuoles (AV) while GO100 and LPS triggered more prominent AV (FIG. 2B). Notably, electron-dense materials within the AV were scarcely present in the LPS group but were abundant in the GO100 group (FIG. 2C), presumably due to the sequestered GO nanosheets.

Beclin 1 and LC3 are two key proteins associated with the autophagy pathway and are common indicators of autophagy induction. LC3 is normally present diffusely in the cytosol but upon autophagy is converted from LC3-I (18 kD) to LC3-II (16 kD), accumulates on the autophagosome membrane and appears as dots. Immunofluorescence microscopy for Beclin 1 and LC3 (FIG. 3A) showed that GO5 and GO100 provoked the appearance of many green dots, which were also observed in the LPS-treated cells but not in the untreated cells. The formation of such large aggregate dots similarly occurred in macrophages treated with large GO (100 µg/ml, FIG. S2B of reference) or treated with dsDNA, and took place in stem cells treated with quantum dots. Quantitative analysis of immunofluorescence micrographs (FIG. 3B) verified that GO100 triggered a significantly higher percentage of cells with LC3+ dots than the untreated, GO5 and LPS groups. Besides, pre-treatment of cells with the autophagy inhibitor 3-methyl adenine (3-MA) diminished the GO100-triggered formation of LC3+ aggregate dots (FIG. S3 of reference). Furthermore, Western blot (FIG. 3C) not only attested that small GO provoked the expression of both Beclin 1 and LC3, but also revealed the emergence of LC3-II, thus confirming the LC3 ligation to autophagosome. These data altogether proved the induction of autophagy in macrophages by large and small GO in a concentration-dependent manner.

GO Treatment of Macrophage Elicited the Cytokine Expression and TLR4/TLR9 Signaling Since the interplay between autophagy and TLRs signaling was recently revealed, we were inspired to explore whether GO elicited TLRs-associated inflammatory responses. ELISA analysis (FIG. 4A-4E) depicted that treatment of macrophage cells with small GO at 100 µg/ml significantly induced the production of IL-2, IL-10, IFN-γ and TNF-α when compared with the untreated cells Such cytokine response was GO concentration-dependent and concurred with the cytokine secretion triggered by LPS. However, treatments of macrophage with small GO at 5 and 100 µg/ml did not elicit the secretion of IFN-β.

Figure 5A:
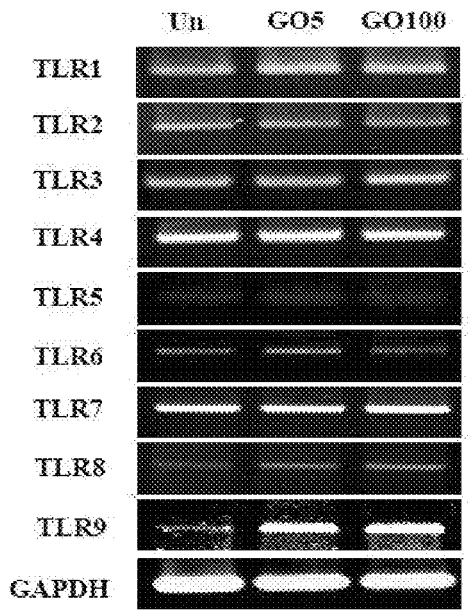
FIG. 5A are RT-PCR analyses illustrating upregulated the transcription of TLRs.
Figure 5B:
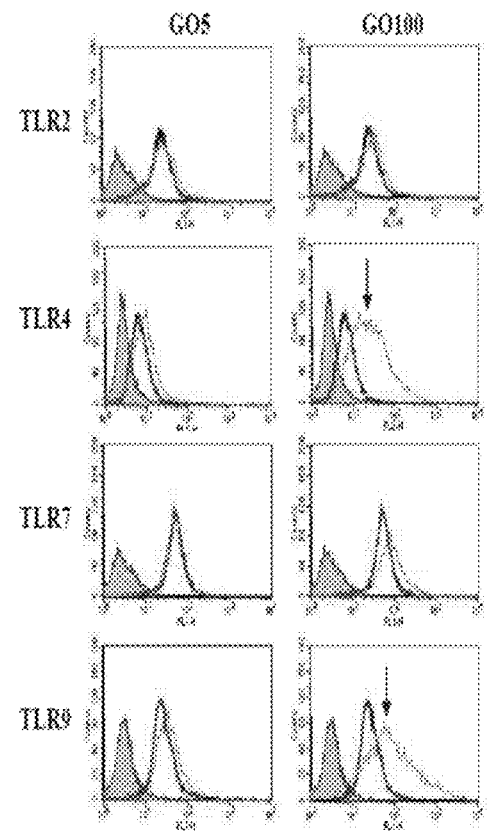
FIG. 5B illustrates expression of TLRs by immunofluorescence labeling coupled with flow cytometry.
Figure 5C:
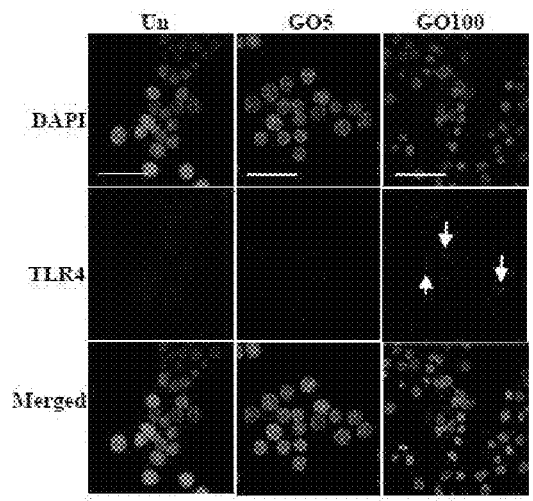
FIG. 5C-5D are immunofluorescence microscopy illustrating upregulation of TLR4 and TLR9.
Figure 5D:
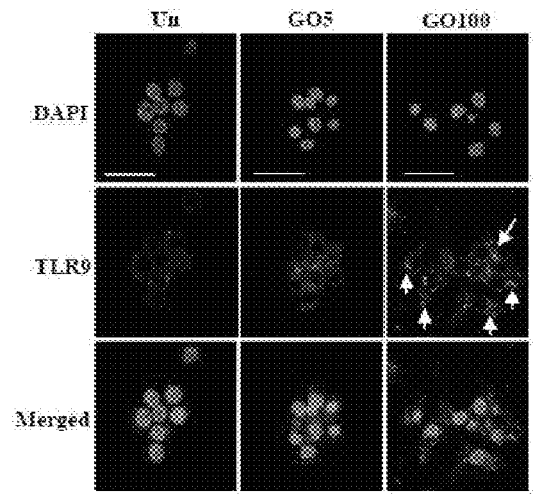

Conversely, GO5 and GO100 evidently upregulated the transcription of TLR9 but barely triggered other TLRs genes, as depicted by RT-PCR analyses (FIG. 5A). Since TLR2, TLR4 and TLR7 also induce autophagy, we further assayed the upregulation of these TLRs in addition to TLR9, by immunofluorescence labeling coupled with flow cytometry. FIG. 5B reveals that GO100 only marginally induced the expression of TLR2 and TLR7, but pronouncedly upregulated the TLR4 and TLR9 expression. The upregulation of TLR4 and TLR9 by GO100 was further confirmed by immunofluorescence microscopy (FIG. 5C-5D). Treatment of macrophage cells with large GO at 100 µg/ml likewise provoked remarkable upregulation of TLR4 and TLR9 (FIG. S4 of reference).

Since only the expression of TLR4 and TLR9 was markedly elicited by GO, we next examined the roles of TLR4 and TLR9 pathways on the inflammatory response. The TLR4 pathway signals through either TRIF or MyD88. The TRIF-dependent pathway results in activation and nuclear translocation of IRF3, thereby triggering the secretion of IFN-α/β. However, GO5 and GO100 neither evoked nuclear translocation of IRF3 (FIG. S5 of reference) nor elicited IFN-β expression (FIG. 4), thus indicating the dispensable role of IRF3.

Conversely, TLR4 signaling through MyD88 leads to the formation of MyD88/IRAK4/TRAF6 signalsome, nuclear translocation of phosphorylated NF-κB and subsequent cytokine expression. TLR9 stimulation recruits MyD88 and results in the formation of MyD88/IRAK4/TRAF6/TRAF3 complex, which relays signals either through IRF7 for IFN-α/β secretion, or through NF-κB for cytokine expression. As demonstrated by the flow cytometry (FIG. 6A-6B) and immunofluorescence microscopy (FIG. 6C-6D), GO100 upregulated the expression of MyD88 and TRAF6 and formation of aggregates indicative of signalsome complex. Concomitantly, GO100 led to the activation and nuclear translocation of phosphorylated NF-κB (FIG. 6E). In conjunction with the cytokine expression downstream of NF-κB signaling (FIG. 4), FIGS. 5 and 6 collectively suggested that GO100 activated the TLR4 and TLR9 signaling cascades.

Inhibition of TLR4/TLR9 Pathways Mitigated the GO-Induced Cytokine Response and Autophagy To confirm the roles of individual signaling mediators on the cytokine response, the macrophage cells were treated with siRNA specific for TLR4, TLR9, MyD88, TRIF or TRAF6. Following the silencing as confirmed by RT-PCR (FIG. 7A-7B), the macrophages cells were incubated with GO100 as in FIG. 4. ELISA analysis (FIG. 7C) depicted that silencing TLR4, TLR9, MyD88 and TRAF6 attenuated the IFN-γ and TNF-α expression with statistical significance (p<0.05) when compared with the control treated with scramble siRNA, thereby attesting the roles of TLR4, TLR9 and their downstream MyD88-dependent pathway in the GO-triggered inflammatory response. In contrast, silencing TRIF did not significantly diminish the IFN-γ and TNF-α expression, nor was IFN-β expression attenuated by silencing these genes (FIG. 7C), thereby suggesting the dispensable role of TRIF-dependent pathway in the GO-triggered innate responses.

Immunofluorescence microscopy (FIG. 7D) further illustrated that silencing TLR4, TLR9, TRIF, MyD88 and TRAF6 abolished the GO-induced formation of Beclin 1 aggregates. Similar inhibition of GO-induced LC3+ aggregates also occurred after silencing TLR4, TLR9, TRIF, MyD88 and TRAF6, as confirmed by immunofluorescence microscopy (FIG. 7E) and quantitative analysis (FIG. 7F). The Western blot (FIG. 7G) further confirmed that silencing these genes suppressed Beclin 1 expression and LC3-I conversion to LC3-II. These data altogether indicated that blockade of TLR4, TLR9 and their downstream MyD88- and TRIF-dependent signaling could abrogate the GO-induced autophagy.

Example 3

GO Induces Autophagy in Different Cancer Cells in a Dose-Dependent Manner

Figure 8A:
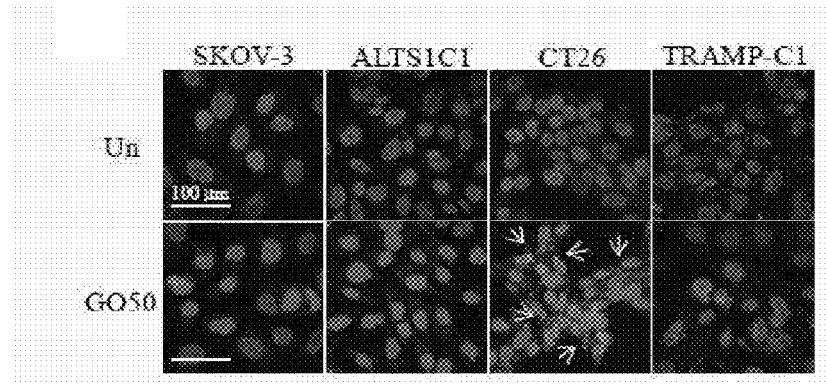
FIG. 8A is immunofluorescence microscopy illustrating responsiveness of cancer cells to GO.
Figure 8B:
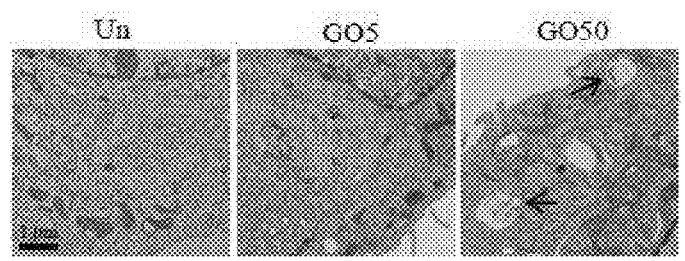
FIG. 8B is transmission electron microscopy (TEM) revealing the formation of autophagic vacuoles and engulfment of GO nanosheets.

To assess the responsiveness of cancer cells to GO, cells of different cancer types including human ovarian carcinoma (SKOV-3), murine astrocytoma (ALTS1C1), murine colon carcinoma (CT26) and murine prostate adenocarcinoma (TRAMP-C1) were cultured in medium supplemented with GO nanosheets (thickness<2 nm, lateral size ≈450 nm in mean diameter). Immunofluorescence microscopy revealed that GO at a concentration of 50 µg/ml (GO50 group) only induced evident autophagy in CT26 cells after 18 h (FIG. 8A), as judged from the appearance of LC3$^+$ punctate dots (which indicates the formation of autophagosomes and hence autophagy). Quantitative analysis of micrographs attested a significantly higher percentage of CT26 cells containing LC3$^+$ dots than other cancer cells, indicating that the GO-induced autophagy is cell type-dependent. Transmission electron microscopy (TEM) further revealed the formation of autophagic vacuoles and engulfment of GO nanosheets (FIG. 8B) while immunofluorescence microscopy illustrated the activation of Beclin1 and p62, thereby confirming the GO-induced autophagy at 50 µg/ml in CT26 cells.

Figure 8C:
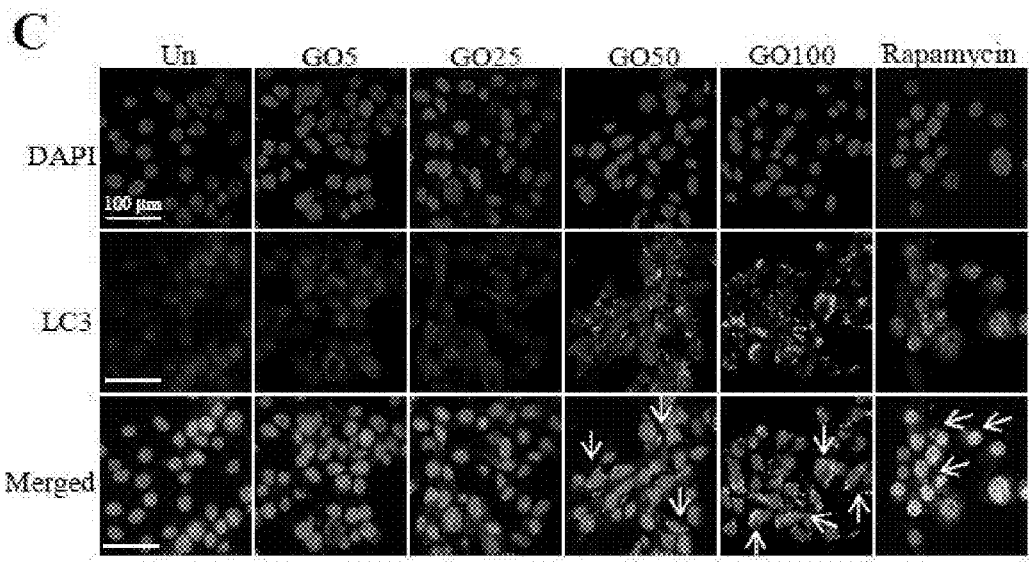
FIG. 8C is a diagram illustrating GO-induced autophagy is dose-dependent in CT26 cells.
Figure 8D:
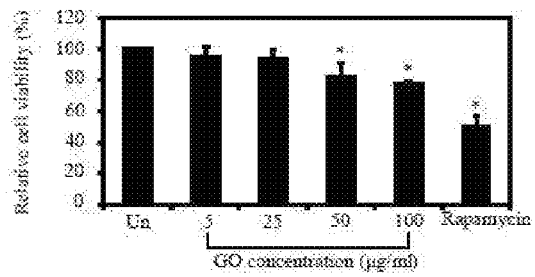
FIG. 8D is a diagram illustrating cell viability of GO50 and GO100 treated cell by MTT assays.
Figure 8E:
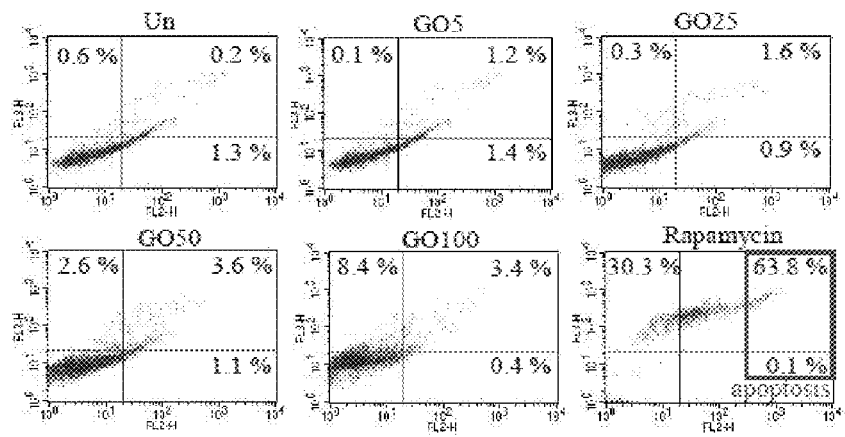
FIG. 8E is a diagram illustrating that no apparent apoptosis or necrosis in CT26 cells even for GO50 and GO100 by PE Annexin V apoptosis analysis.
Figure 8F:
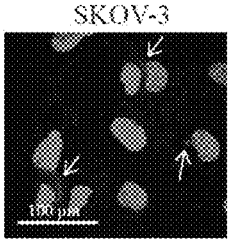
FIG. 8F is immunofluorescence microscopy illustrating responsiveness of cancer cells to GO.
Figure 8F:
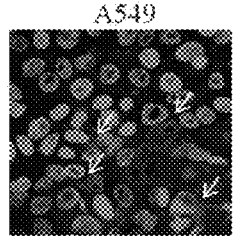
Figure 8F:
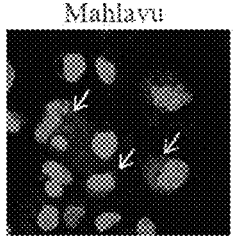
Figure 8F:
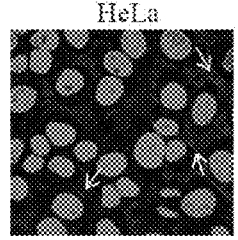

The GO-induced autophagy was also dose-dependent in CT26 cells (FIG. 8C). GO at 100 µg/ml (GO100) also elicited apparent autophagy in such cancer cells as SKOV-3, A549, mahlavu and HeLa (FIG. 8F). In comparison with untreated cells, GO50 and GO100 resulted in reduced cell viability as judged from MTT assays (FIG. 8D), yet PE Annexin V apoptosis analysis (FIG. 8E) and mitochondrial membrane potential analysis (not illustrated) revealed no apparent apoptosis or necrosis in CT26 cells even for GO50 and GO100.

GO Activates TLR-4/9 Pathways in CT26 Cells.

Figure 9A:
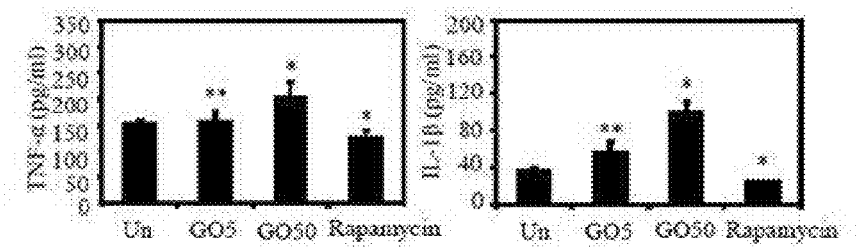
FIG. 9A is a diagram illustrating that GO50 significantly provoked the production of TNF-α and IL-1β when compared with the untreated cells.
Figure 9B:
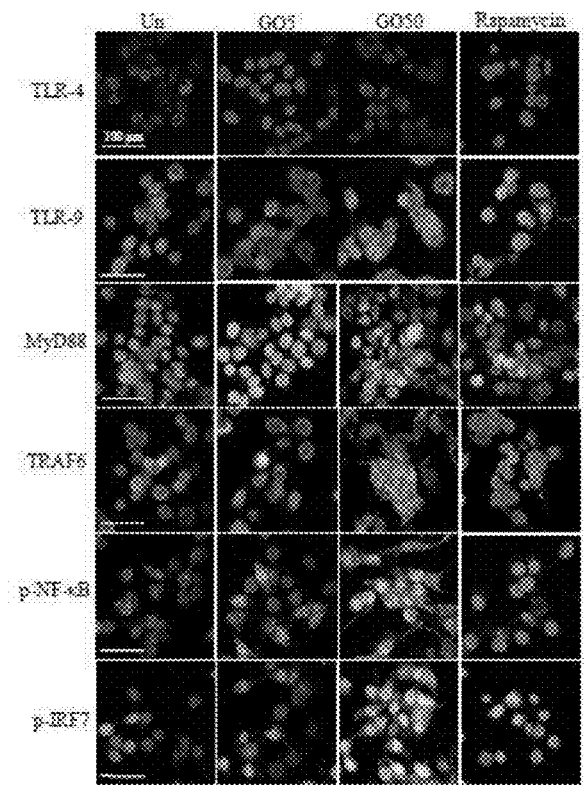
FIG. 9B is immunofluorescence microscopy demonstrating that GO50, but not rapamycin, simultaneously activated TLR-4, TLR-9, MyD88 and TRAF6 and enhanced the phosphorylation of NF-κB and IRF7.

Owing to the findings that GO provokes both TLR-4 and TLR-9 signaling pathways in macrophage cells in vitro, we surmised that GO also triggered TLR-4/9 cascades and their downstream cytokine (e.g. TNF-α and IL-1β) production in CT26 cells. Indeed, GO50 significantly provoked the production of TNF-α and IL-1β when compared with the untreated cells (FIG. 9A). Flow cytometry (not illustrated) and immunofluorescence microscopy (FIG. 9B) demonstrated that GO50, but not rapamycin, simultaneously activated TLR-4, TLR-9, MyD88 and TRAF6 and enhanced the phosphorylation of NF-κB and IRF7. Since MyD88, TRAF6 and NF-κB are signaling mediators shared by TLR-4 and TLR-9 pathways while IRF7 mediates the TLR-9 cascade, these data proved the elicitation of TLR-4 and TLR-9 pathways by GO50. However, neither GO5 nor rapamycin apparently activated both pathways.

GO was phagocytosed by CT26 cells in a way related to TLR-4/9 signaling.

Figure 9C:
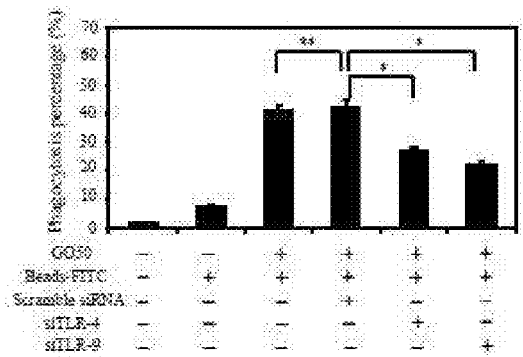
FIG. 9C is a diagram illustrating GO was taken up by CT26 cells via phagocytosis.

TLR-4 is a receptor on the cell surface whereas TLR-9 is produced in ER and translocates to endosome. To explore how GO entered the cells to engage TLR-9, we treated CT26 cells with FITC-conjugated beads as a marker of phagocytosis. Comparison of the cells treated with beads only with the cells co-treated with beads and GO50 (FIG. 9C) revealed that GO was taken up by CT26 cells via phagocytosis. To explore whether the phagocytosis was associated with TLRs signaling, CT26 cells were transfected with small interfering RNA (siRNA) specific for tlr4 (siTLR-4) or tlr9 (siTLR-9), which downregulated the expression of TLR-4 and TLR-9, respectively, and significantly attenuated the GO-induced production of TNF-α and IL-1β. siTLR-4 and siTLR-9 also markedly abrogated the phagocytosis of GO50 (FIG. 9C), suggesting that TLR-4 and TLR-9 played a role in the uptake of GO.

Figure 9D:
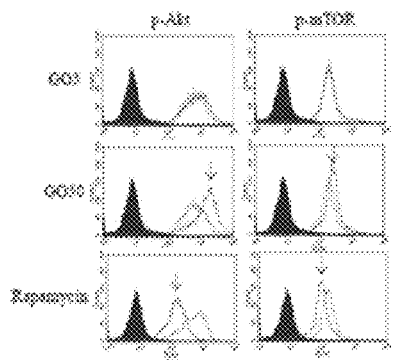
FIG. 9D is a diagram illustrating that rapamycin suppressed the phosphorylation of Akt and mTOR and GO50 enhanced the phosphorylation of Akt and mTOR.
Figure 9E:
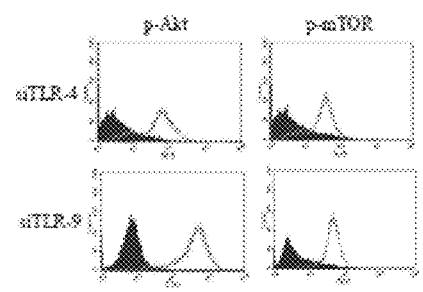
FIG. 9E is a diagram illustrating that the phosphorylation of Akt and mTOR was barely altered regardless of TLR-4/9 knockdown prior to GO50 treatment.

GO-induced TLR-4/9 cascades were independent of the mTOR pathway.

mTOR is a negative autophagy regulator, and repressing the phosphorylation of mTOR and its upstream Akt can elicit autophagy. Indeed, rapamycin suppressed the phosphorylation of Akt and mTOR (FIG. 9D) and induced autophagy (FIG. 8C). However, GO50 enhanced the phosphorylation of Akt and mTOR (FIG. 9D), suggesting that the GO-induced autophagy proceeded through a pathway unrelated to mTOR. Conversely, the phosphorylation of Akt and mTOR was barely altered regardless of TLR-4/9 knockdown prior to GO50 treatment (FIG. 9E), indicating that the GO-induced TLR-4/9 pathways were independent of the mTOR pathway.

GO-induced TLR4/9 signaling was upstream of the GO-induced autophagy.

Figure 9F:
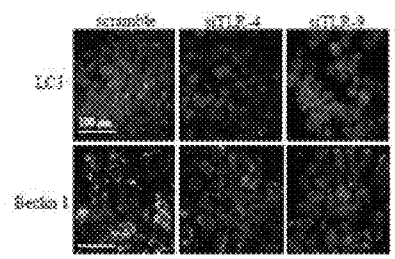
FIG. 9F-9G are immunofluorescence microscopy and diagram illustrating that siTLR-4 and siTLR-9 significantly mitigated the GO-induced activation of LC3 and Beclin 1.
Figure 9G:
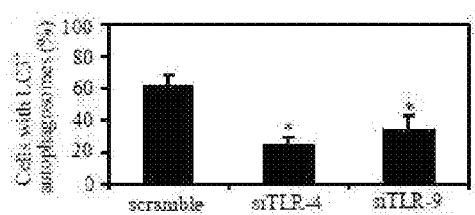

The interplay between autophagy and immunity has drawn intensive attention in recent years. It was shown that TLR-4 signaling can activate autophagy in a way dependent on ATG5 and Beclin 1. Oppositely, it was also suggested that autophagy regulates the activation of TLRs pathways. To elucidate the crosstalk between the GO-induced TLR-4/9 signaling and autophagy, CT26 cells were transfected with siTLR-4 or siTLR-9, followed by GO50 treatment. Compared with the scrambled siRNA, siTLR-4 and siTLR-9 significantly mitigated the GO-induced activation of LC3 and Beclin 1 (FIG. 9F-9G), proving that TLR-4/9 regulated the GO-induced autophagy.

Figure 10A:
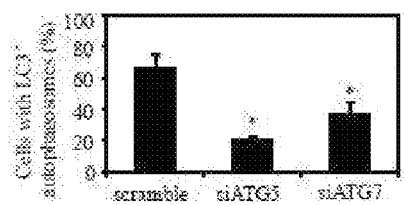
FIG. 10A is a diagram illustrating transfected cells with siRNA for atg5 and atg7 to knockdown the GO-induced autophagy.
Figure 10B:
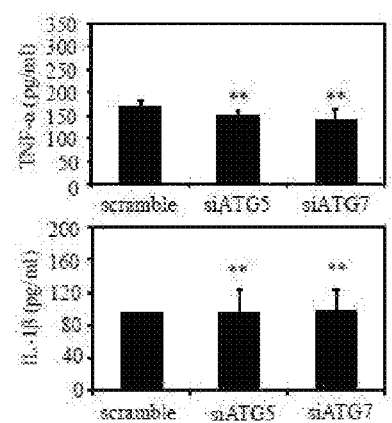
FIG. 10B-10D are diagrams illustrating inhibition of GO-induced autophagy by siATG5 or siATG7 neither abolished the GO-induced production of TNF-α and IL-1β (FIG. 10B) nor affected the expression of TLR-4 and TLR-9 upon GO50 treatment (FIG. 10C-10D)
Figure 10C:
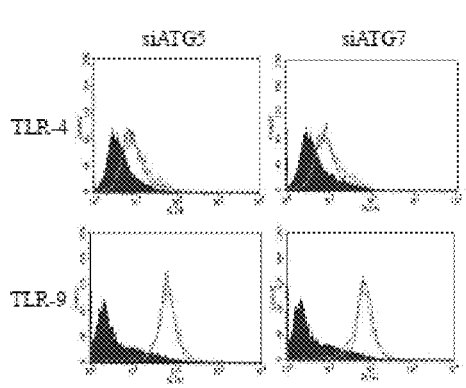
Figure 10D:
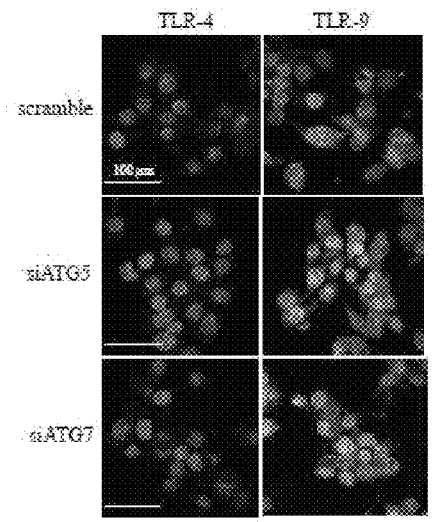

To evaluate whether the opposite was true, we transfected cells with siRNA for atg5 and atg7 (genes essential for autophagy induction) to knockdown the GO-induced autophagy (FIG. 10A). The inhibition of GO-induced autophagy by siATG5 or siATG7 neither abolished the GO-induced production of TNF-α and IL-1β (FIG. 10B) nor affected the expression of TLR-4 and TLR-9 upon GO50 treatment (FIG. 10C-10D), thus autophagy did not regulate the GO-induced TLR-4/9 signaling. These data collectively attested that GO-activated TLR-4/9 signaling was upstream of autophagy.

Beclin 1 is inactivated by the inhibitory interaction with TAB2/3, Bcl-2 and Bcl-xL in the usual state and TLR signaling can release Beclin 1 from the inhibitory molecules, enhance the interaction between Beclin 1 and MyD88, while activated TRAF6 stimulates Beclin 1 to initiate autophagy. Since GO50 induced TLR-4/9 and downstream signaling effectors MyD88 and TRAF6, and concurrently activated LC3, Beclin 1 and the ensuing autophagy, we propose that GO engagement of TLR-4/9 activates MyD88/TRAF6 and induces autophagy through the activation of Beclin 1 and LC3, in a way independent of the mTOR pathway.

Figure 11A:
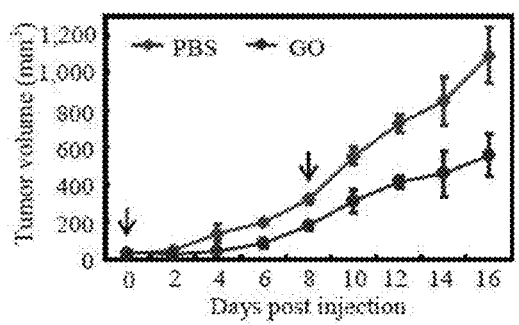
FIG. 11A-11B are diagrams illustrating that GO alone significantly suppressed the tumor progression without considerably compromising the body weight.
Figure 11B:
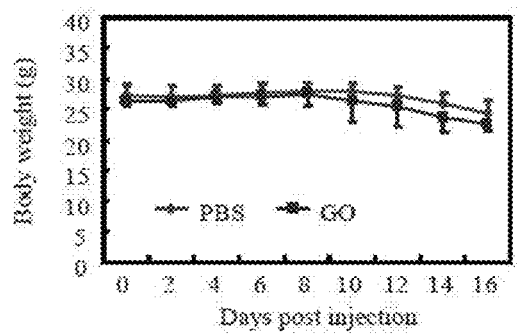
Figure 11C:
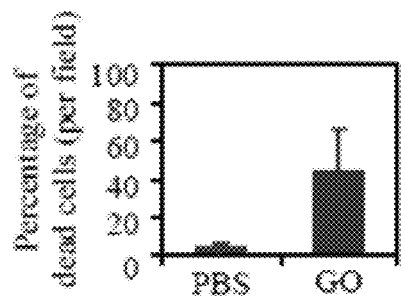
FIG. 11C is a Live/Dead assay diagram illustrating analysis of the tumor sections 5 days after GO injection.
Figure 11D:
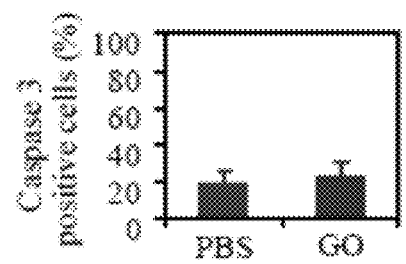
FIG. 11D is a diagram illustrating that no apparent apoptosis or necrosis was observed in GO50.
Figure 11E:
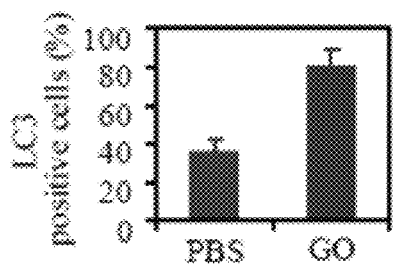
FIG. 11E is a diagram illustrating LC3+ aggregation in GO50.
Figure 11F:
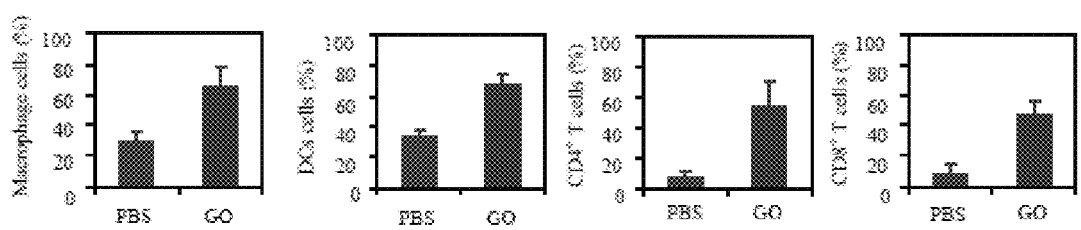
FIG. 11F is a diagram illustrating that GO50 remarkably potentiated the infiltration of macrophage, dendritic cells (DCs), CD4+ and CD8+ T cells into the tumor bed.

GO Injection Suppressed Tumor Formation, Enhanced Cell Death, Autophagy and Immune Cell Infiltration To assess the potential of GO-induced autophagy in cancer therapy, CT26 cells were injected subcutaneously into BALB/c mice, followed by intratumoral injections of PBS or GO at day 0 (when the tumor volume reached $\approx$30-40 mm$^3$) and day 8. In comparison with PBS, GO alone significantly suppressed the tumor progression (FIG. 11A) without considerably compromising the body weight (FIG. 11B). Analysis of the tumor sections 5 days after GO injection revealed pronounced cell death as confirmed by Live/Dead assay (FIG. 11C). However, no apparent apoptosis was observed at day 5 (FIG. 11D). GO alone also induced autophagy as evidenced by the considerable LC3$^+$ aggregation (FIG. 11E). Strikingly, GO50 remarkably potentiated the infiltration of macrophage, dendritic cells (DCs), CD4$^+$ and CD8$^+$ T cells into the tumor bed (FIG. 11F). Analysis of the tumor sections at the endpoint revealed significant cell death, apoptosis, autophagy induction and infiltration of immune cells within the tumors. The concurrent induction of autophagy and enhanced immune cell infiltration indicate that GO alone is sufficient to potentiate the antitumor immune responses.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A method of activating a Toll-like receptor in a cell, comprising:
   contacting the cell with graphene oxide in an amount effective to activate at least one of TLR-2 (Toll-like receptor 2), TLR-4 (Toll-like receptor 4), TLR-7 (Toll-like receptor 7) and TLR-9 (Toll-like receptor 9) in the cell, whereby at least one of TLR-2, TLR-4, TLR-7 and TLR-9 are activated in the cell.

2. The method as claimed in claim 1, wherein the cell is an immune cell.

3. The method as claimed in claim 1, wherein TLR-4 and TLR-9 are both activated in the cell.

4. The method as claimed in claim 1, wherein the particle sizes of the graphene oxide range from 100 nm to 3 µm.

5. The method as claimed in claim 1, wherein the particle sizes of the graphene oxide range from 100-800 nm.

6. The method as claimed in claim 1, wherein the concentration of the graphene oxide is greater than or equal to 5 µM.

7. The method as claimed in claim 1, wherein the concentration of the graphene oxide is greater than or equal to 100 µM.

8. The method as claimed in claim 1, wherein the cell reveals no apparent apoptosis or necrosis after treatment with the graphene oxide.

9. The method as claimed in claim 1, wherein the cell expresses both of TLR-4 and TLR-9.

* * * * *